(12) United States Patent
McCauley et al.

(10) Patent No.: US 8,308,854 B2
(45) Date of Patent: Nov. 13, 2012

(54) HELIUM RECLAMATION SYSTEMS AND METHODS FOR A GAS CHROMATOGRAPH

(75) Inventors: Edward B. McCauley, Cedar Park, TX (US); Matt A. Lasater, Pflugerville, TX (US)

(73) Assignee: Thermo Finnigan LLC, San Jose, CA (US)

( * ) Notice: Subject to any disclaimer, the term of this patent is extended or adjusted under 35 U.S.C. 154(b) by 345 days.

(21) Appl. No.: 12/638,274

(22) Filed: Dec. 15, 2009

(65) Prior Publication Data
US 2011/0138877 A1    Jun. 16, 2011

(51) Int. Cl.
*B01D 53/02* (2006.01)
(52) U.S. Cl. ............ 96/101; 96/4; 96/102; 96/105; 96/108; 96/144; 96/146; 95/45; 95/82; 95/89; 73/23.42
(58) Field of Classification Search ............ 96/4, 10, 96/101, 105, 106, 102, 108, 143, 144, 146; 95/45, 82, 89; 73/23.35, 23.41, 23.42
See application file for complete search history.

(56) References Cited

U.S. PATENT DOCUMENTS

| 3,520,171 | A |   | 7/1970  | Amati et al. |         |
|-----------|---|---|---------|--------------|---------|
| 4,104,005 | A | * | 8/1978  | Poirier      | 417/394 |
| 4,230,464 | A |   | 10/1980 | Bonmati et al. |       |
| 5,183,072 | A |   | 2/1993  | Pengler      |         |
| 5,707,424 | A | * | 1/1998  | Tom et al.   | 95/95   |
| 6,063,166 | A |   | 5/2000  | Wilson       |         |
| 6,074,461 | A |   | 6/2000  | Wilson       |         |
| 6,293,995 | B2 | * | 9/2001 | Wilson       | 95/23   |
| 6,929,678 | B2 |   | 8/2005 | Hartlein     |         |
| 7,204,679 | B2 | * | 4/2007 | Wheeler      | 417/390 |
| 7,384,453 | B2 | * | 6/2008 | Bostrom et al. | 95/82 |
| 2007/0125233 | A1 |  | 6/2007 | Bostrom et al. |      |

FOREIGN PATENT DOCUMENTS

JP    2003 071231    3/2003

(Continued)

OTHER PUBLICATIONS

Donald J. Bowe, "Helium Recovery and Recycling Makes Good Business Sense," Industrial Heating (2004), pp. 79-81. http://wwvv.airproducts.com/NR/rdonlyres/F9D0CAA5-2A67-413B-A71F-54C72CD46E67/0/ IHHeRecoveryArticlefinal.pdf.

(Continued)

*Primary Examiner* — Robert Clemente
(74) *Attorney, Agent, or Firm* — Thomas F. Cooney (57) ABSTRACT

A system for recycling helium carrier gas comprises: a bladder, the bladder interior fluidically configured so as to receive helium-bearing gas output from at least one of a split vent and a septum purge vent of a gas chromatograph; a compartment containing the bladder; a source of pressurized air or gas operable so as to supply pressurized air or gas into the compartment interior so as to compress the bladder containing the helium-bearing gas; a gas reservoir fluidically coupled to the bladder interior so as to receive the helium bearing gas from the compressed bladder interior; and at least one gas purification module configured so as to receive the helium-bearing gas from the gas reservoir and operable to remove contaminants from the helium-bearing gas, an output of the at least one gas purification module being fluidically coupled to a carrier gas inlet of the gas chromatograph.

12 Claims, 7 Drawing Sheets

FOREIGN PATENT DOCUMENTS

WO     WO 98/36815 A1     8/1998

OTHER PUBLICATIONS

Edmund T. Lewis et al., "Fundamentals of Purge and Trap," Teledyne Instruments, Application Note (2003), http://www.ingenieria-analitica.com/LlocIA1/PDF/TEKMAR_JL04/61_Fundamentals of Purge and Trap.pdf, pp. 1-2.

RESTEK CORP., "Optimizing the Analysis of Volatile Organic Compounds," Technical Guide (Abridged), https://www.chromspec.com/pdf/lit/rk08.pdf, 2003, pp. 1-30.

\* cited by examiner

HELIUM RECLAMATION SYSTEMS AND METHODS FOR A GAS CHROMATOGRAPH

BACKGROUND OF THE INVENTION

Gas chromatography is a well-known method for identifying the chemical composition of a material sample and has found application in a variety of industries which rely on the identification of chemical compounds. The gas chromatography process involves vaporizing and introducing a material sample into a chromatographic column, wherein the material sample is transported through the column by the flow of an inert, gaseous carrier, such as nitrogen ($N_2$), hydrogen ($H_2$) or Helium (He).

Modern gas chromatographs typically utilize fused silica capillary columns to effect separation of the sample material. When using such columns, it is often necessary to split much of the sample in order to avoid detector saturation or phase saturation of the column, or to split much of the supplied gas in order to avoid elevated baselines caused by residual solvent vapor or low vapor pressure matrices e.g. oils. In effect, the majority of consumed gas is not directly involved with the chromatography, and is exhausted to the atmosphere. For instance, a typical gas chromatograph splits 50 ml/min or more of gas and utilizes, perhaps only 1 ml/min chromatographically, corresponding to a split ratio of 50:1. Accordingly, such a chromatograph will vent 50 times the amount of gas actually required to carry a sample through a chromatograph column for an analysis. An automated feature found on many gas chromatographs typically referred to as "gas saver" allows setting lower split flows following an injection in order to conserve gas. While the gas saver feature results in consuming lower amounts of helium, it is known that there is a tradeoff between using low split flows and the subsequent contamination level (e.g. elevation of baselines) which ensue. It is therefore analytically desirable to maintain higher split flows, yet economically desirable to use lower ones. It is therefore desirable to use high split flows of 50 standard cubic centimeters per minute (sccm) or greater, and provide a means for recycling the majority of spent gas.

There have been some descriptions of systems that employ carrier gas recycling. For example, U.S. Pat. No. 4,230,464, issued in the names of inventors Bonmati et al., describes an industrial scale preparative chromatograph using high gas flow rates and large quantities of carrier gas (between 5 and 200 cubic meters of carrier gas per hour). The purification applies to the gas which has been used for the chromatographic process of a large scale physical separation and purification of known constituents (as opposed to a laboratory analysis setting, which is directed towards identifying and quantifying trace chemical constituents in widely varying matrices). U.S. Pat. No. 6,063,166, issued in the name of inventor Wilson, describes closed loop recirculation of hydrogen gas in a system utilizing metal hydride storage systems. United States Patent Application Publication 2007/0125233 A1, in the names of inventors Bostrom et al., describes field portable "down hole" instruments for in-situ analysis of subterranean fluids, that uses fixed-temperature metal hydride reservoirs as sources and storage reservoirs of carrier gas. U.S. Pat. No. 6,074,461, issued in the name of inventor Wilson, teaches the use of gas recycling systems coupled to chromatographs, wherein the recycling systems include first and second stages for effecting respective tasks of carrier gas purification and carrier gas pressurization. Wilson further notes that the gas purification stage may be designed according to the particular carrier gas operable in the particular embodiment of the chromatograph and may include a packed trap, such as molesieve, a membrane or similar device permeable only by hydrogen, a helium getter, a packed bed trap designed for cleaning helium optimized for another carrier gas, or a polymer barrier that is efficient for transmitting only helium. The aforementioned gas purification methods of the prior art suffer from inefficiency and poor scalability in the case of Bonmati et al. and suffer from cost, complexity, analytical deficiencies and/or safety in the cases of Bostrom et al. and Wilson. Such is the case when considering a recycling system based on hydrogen.

Hydrogen, when used as a gas chromatograph carrier gas, presents a potential fire or explosion hazard and is associated with some other analytical deficiencies. It is known, for example, that, if hydrogen carrier gas is employed for gas chromatography/mass spectrometry (GCMS) applications, sensitivity is reduced and adverse chemical reactions in the inlet (e.g. hydrogenation) or the ion source (e.g. de-hydrohalogenation) can occur. Therefore, for many routine laboratory or field-based analytical purposes, it is desirable to use helium exclusively as the carrier gas. Unfortunately, the increasing cost of helium is resulting in the use of this gas as a carrier for gas chromatography to become prohibitively expensive, particularly in some developing countries where, for instance, up to 500 Euros may be spent on a single cylinder of gas. Traditional methods of gas purification described in the prior art (e.g. helium gettering) utilize reactive metal alloys for ensuring removal of trace contaminants from otherwise pure helium. This technique is impractical for scrubbing multiple microliter quantities of solvents due to the limited capacity and non-reversible chemical reactions which occur in these types of traps. Likewise, molecular sieve traps of conventional design are ubiquitously employed and useful for removal of trace contaminants which are strongly adsorbed, but lighter, more-weakly-bound chemicals can break through the traps in relatively short time intervals unless large quantities of adsorbents are utilized, or cryogenic conditions are maintained around the trap. Due to the high cost of synthetic porous polymers, large-capacity in-line traps of this nature are therefore also impractical.

The compression cycle involved for recompression of the recycled gas stream is necessarily a closed loop system so as to prevent the introduction of atmospheric gasses which would otherwise contaminate the gas stream. Prior art pumping systems which employ dedicated rotary vane pumps, piston pumps etc. have the disadvantage of cost and the propensity to introduce hydrocarbon contaminants into the gas stream due to the need for oil based lubricants. Additionally, these pumps are free running type pumps which impose a vacuum on the gas harvesting side of the pump. Without special modifications to the electronic pressure control of the gas chromatograph to deal with the reduced pressure, or without providing a complex means of throttling the flow delivered to the pump, these methods are unusable for existing installations of GC and GCMS units.

Thus, it is further desirable to employ a helium reclamation and recycling system in most existing routine laboratory or field-based chromoatographs. To increase portability and versatility and reduce operating costs as much as possible, the helium reclamation and recycling system should (a) be readily adaptable to virtually any analytical gas chromatograph system without interference in the normal operation of the chromatograph system (b) should include provisions for periodical self analysis of the purity of the reclaimed helium and (c) should allow re-generation of the cleansing qualities of the reclamation system so that large quantities of sorbents are not needed. The present invention addresses such needs.

SUMMARY

This disclosure provides methods and systems that enable the collection of relatively pure split gas helium during and following a gas chromatograph injection cycle. These methods and systems can enable a cylinder of helium to last up to several years without replacement. For example, an exemplary system in accordance with the present teachings collects helium (together with residual solvent and analytes) at substantially atmospheric pressure from the split vent and septum purge output of a gas chromatograph, re-compresses the collected gas, purifies the helium to a suitable purity, and re-introduces the purified gas upstream of the gas chromatograph.

A collection and re-compression portion of a system in accordance with the present teachings may include a gas barrier bag comprising a membrane material housed inside a bag containment vessel. Preferably, the membrane material comprises a flexible gas barrier material such as Tedlar® or more preferably a low permeability metal foil-polymer laminate film such as PAKVF4 from sorbentsystems.com. Inflation of the bag with the gasses collected from the split vent and septum purge output allows collection of helium at substantially atmospheric pressure following an injection time period. This allows collection during the time interval following an injection where column head pressure is critical in order to maintain correct column flow, but split flow is not. Collection at near atmospheric pressure also allows systems disclosed herein to be utilized on existing gas chromatographs without undue modifications of any split and purge controls of the gas chromatograph. With the bag subsequently isolated from the split vent and septum purge outlets by a valve, a low cost air compressor or house air supply is used to pressurize the containment vessel so as to effect gas compression of the membrane. The gas bag compression causes the collected gas portion to be transferred to a reservoir through a one-way check valve. The containment vessel can be vented of compressed air into a noise suppressor and the cycle repeated as necessary. The compressor and valve operation can be configured to be activated optically or via a reed switch or contact switch in proximity to the membrane. Alternatively, a simple timer mechanism can be set to intermittently compress the membrane consistent with the established gas flow.

In some embodiments, a purification portion of the system may incorporate a pyrolysis furnace, possibly employing a metal catalyst, that may be employed to ensure residual contaminants are reactively converted to non-interfering low molecular weight compounds. In some embodiments, the purification portion may include a molecular sieve trap and the system may include provisions for backflushing the trap with fresh helium so as to prevent trap breakthrough and ensure that residual contaminants such as permanent gasses cannot accumulate in the gas stream. Advantageously, the system configurations disclosed herein enable self examination of the gas purity or identification of trap breakthrough by monitoring the purity of the reclaimed carrier gas with the gas chromatograph and/or mass spectrometer.

BRIEF DESCRIPTION OF THE DRAWINGS

The above noted and various other aspects of the present invention will become apparent from the following description which is given by way of example only and with reference to the accompanying drawings, not drawn to scale, in which.

DETAILED DESCRIPTION

Figure 2A:
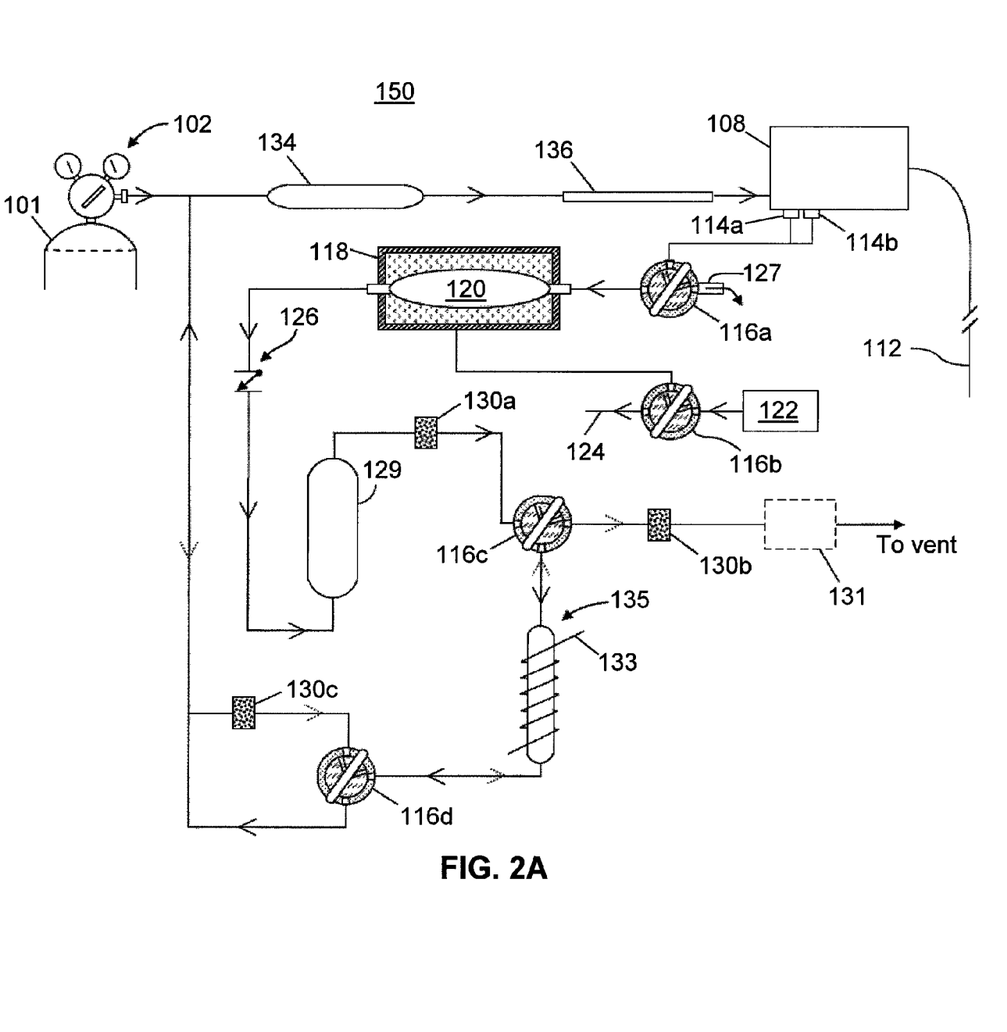
FIG. 2a is a schematic illustration of a second gas chromatograph system having helium reclamation and recycling capability in accordance with the present teachings.
Figure 2B:
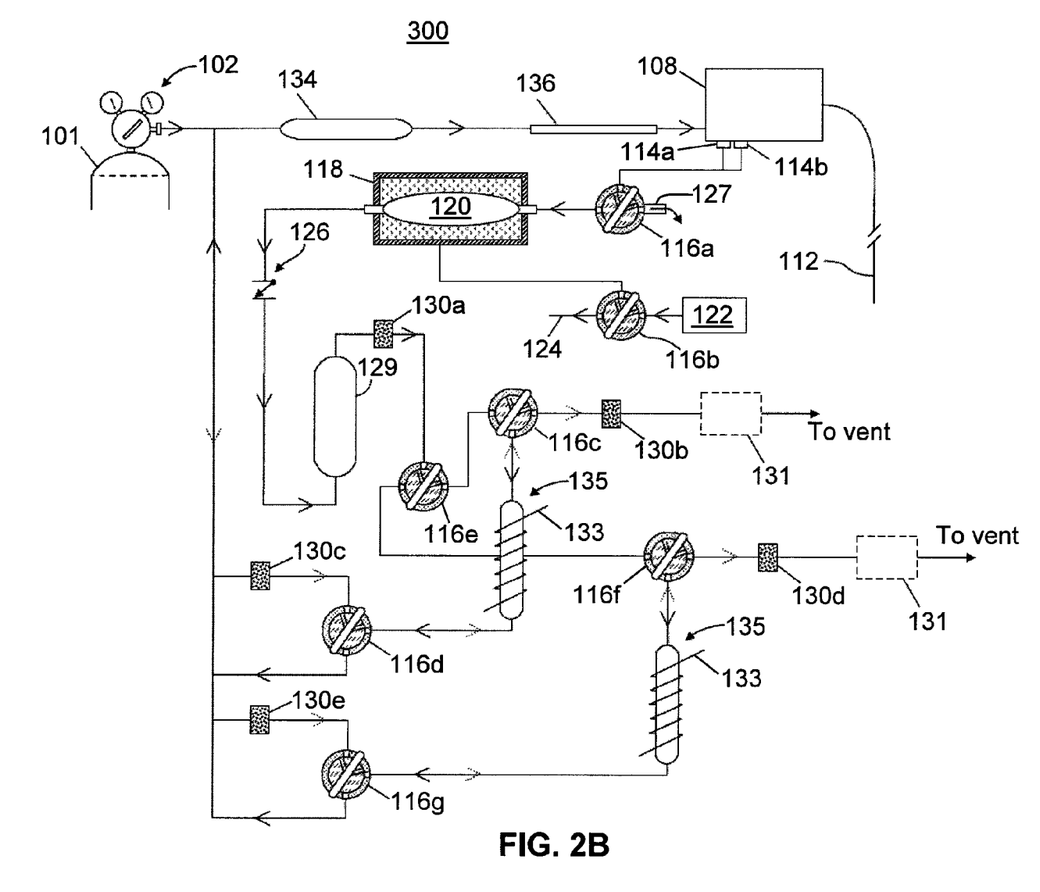
FIG. 2b is a schematic illustration of a third gas chromatograph system having helium reclamation and recycling capability in accordance with the present teachings.
Figure 3:
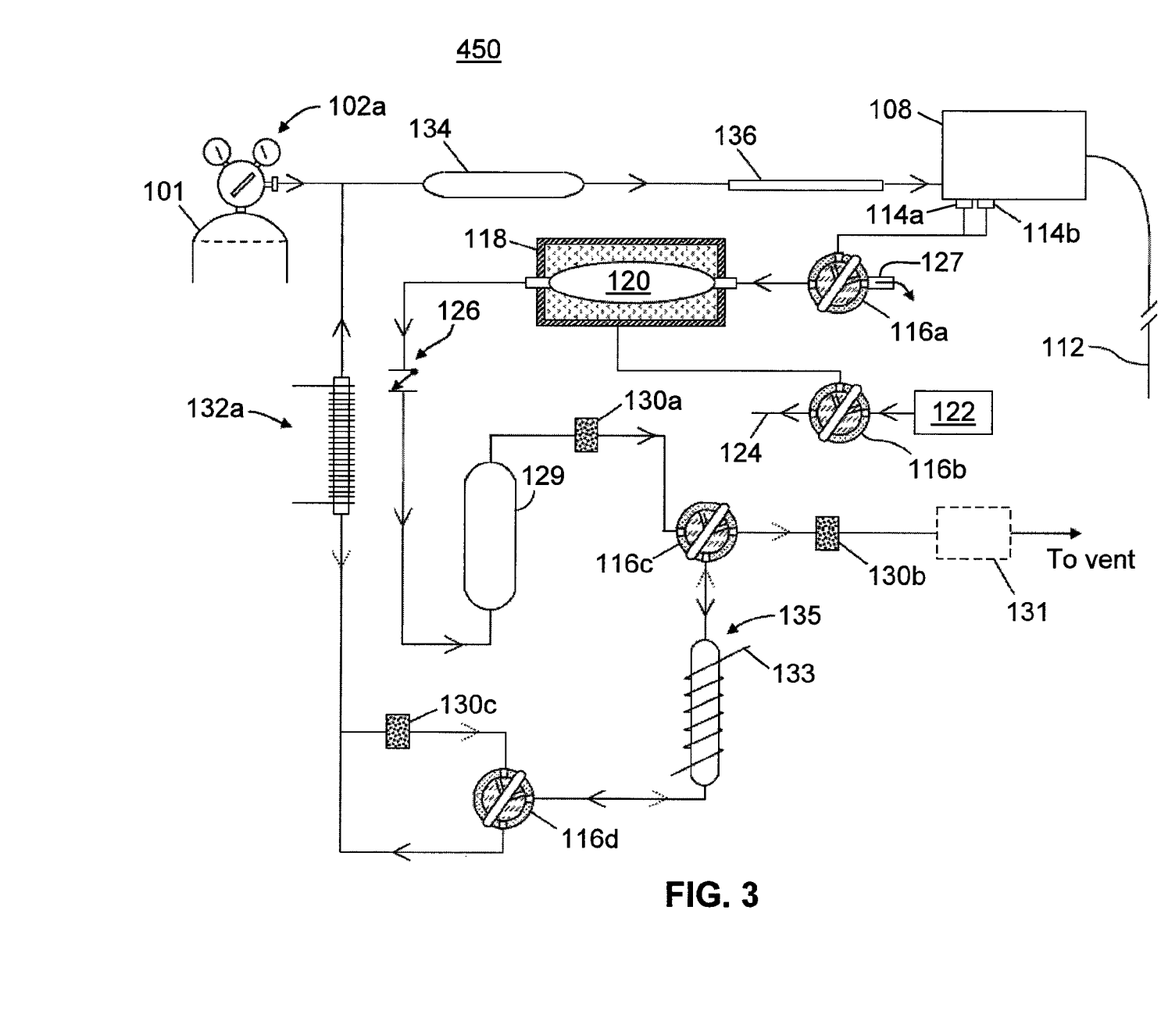
FIG. 3 is a schematic illustration of a fourth gas chromatograph system having helium reclamation and recycling capability in accordance with the present teachings.

The following description is presented to enable any person skilled in the art to make and use the invention, and is provided in the context of a particular application and its requirements. Various modifications to the described embodiments will be readily apparent to those skilled in the art and the generic principles herein may be applied to other embodiments. Thus, the present invention is not intended to be limited to the embodiments and examples shown but is to be accorded the widest possible scope in accordance with the features and principles shown and described. The particular features and advantages of the invention will become more apparent with reference to the appended FIGS. 1-6, taken in conjunction with the following description. In these drawings, it is to be noted that lines connecting various labeled components represent gas pathways or lines that may be physically embodied by various tubes or capillaries and that solid-line arrows drawn on such gas lines represent gas flow during normal chromatograph operation or during operation of the gas reclamation components. Dotted-line arrows in FIGS. 1-3 represent the flow of helium during backflushing, as described later herein.

Figure 1:
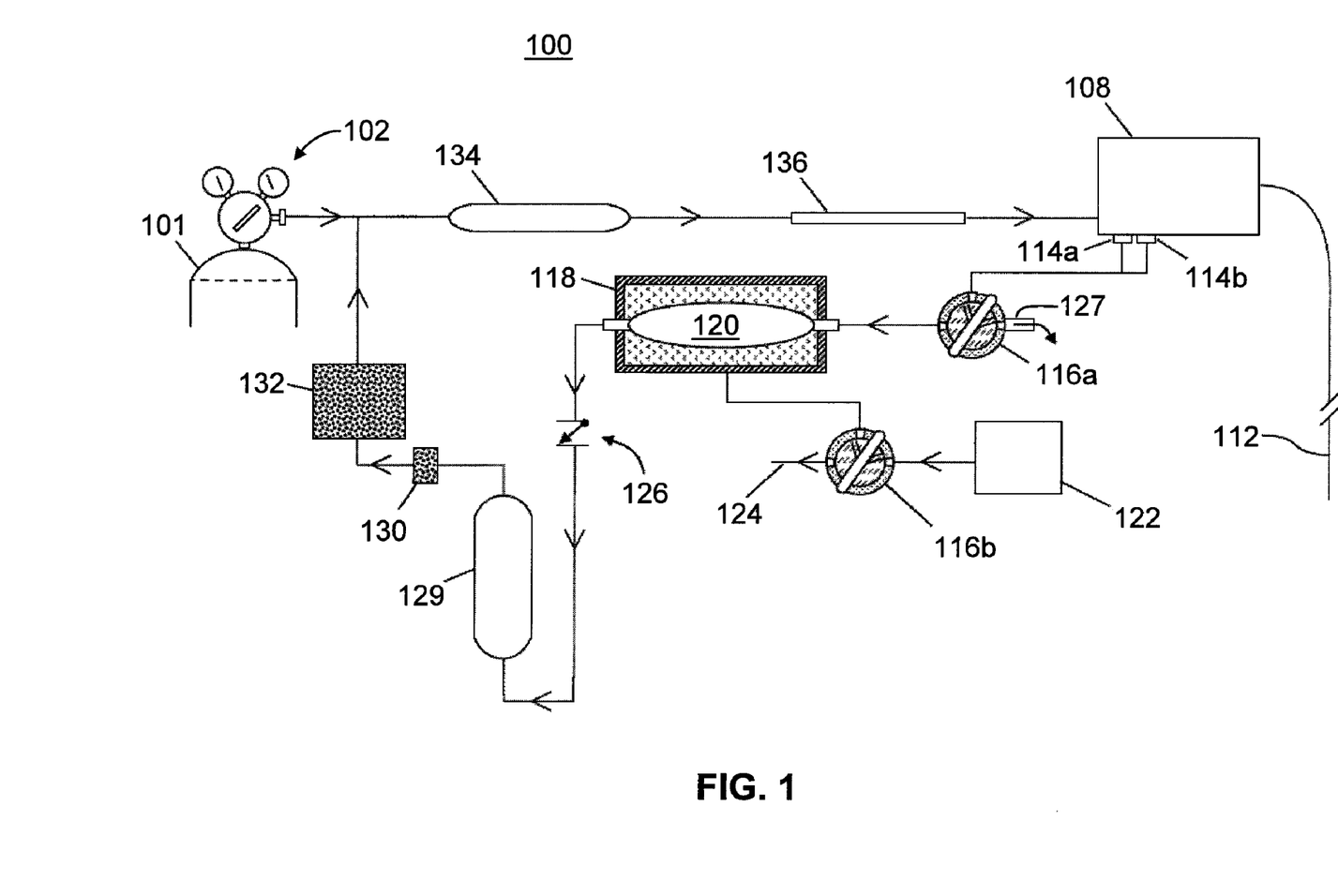
FIG. 1 is a schematic illustration of a first gas chromatograph system having helium reclamation and recycling capability in accordance with the present teachings.

A first helium reclamation and recycling system 100 in accordance with the present teachings is illustrated in FIG. 1. A main helium gas supply 101 outfitted with a pressure regulator 102 initially provides purified helium carrier gas to an inlet port (generally, an injector) of a gas chromatograph 108. (For purposes of simplicity, only the pneumatic control unit of said chromatograph is illustrated.) Since commercially obtained ultra-high-purity gas can contain up to 10 parts-per-million of trace components, a combined trap 134 and, possibly, an oxygen indicating trap 136 may be included in conventional manner between the gas supply 101 and the gas chromatograph 108 in order to remove traces of water, oxygen and hydrocarbons. In known fashion, the gas chromatograph 108 causes a sample gas (not shown) to be mixed with a large excess of the helium carrier gas and causes a fraction of the resulting mixture (in the case of split injections) or the near totality of it (for splitless injections) to be directed to a chromatographic column 112 during an injection period. The sample gas may contain an analyte gas admixed with volatile solvent gases. The chromatographic column may output to a mass spectrometer (not shown) having an ion source for ionizing the sample gas.

As is commonly the case, the gas chromatograph system 108 may divide the carrier gas flow into three portions: a first portion which is used to propel the sample material through the chromatographic column 112, a second portion which is used to purge an inlet septum (not shown) of the chromatograph inlet system, and a third portion that is used to carry away excess sample material (in the case of a split injection) or residual solvent vapor (in the case of a splitless injection). The second and third portions, which in combination are often, as noted above, volumetrically many times in excess of the portion delivered to the column 112, are output from the chromatograph system 108 by means of a septum purge vent 114a and split vent 114b, respectively. In the absence of a carrier gas reclamation system, these second and third portions of the carrier gas are lost from the system.

The remaining components of the system 100 comprise the helium carrier gas reclamation components. As illustrated in FIG. 1, the combined output of the split and purge vents is collected and directed to a bladder 120. The bladder 120 may alternatively be referred to as a "collection bag". The flow of the split/purge gas into the bladder 120 may be controlled by a first 3-way valve 116a installed between the gas chromatograph split and purge vents and the bladder. In a first configuration, the first valve 116a directs the split/purge gas into the bladder which inflates as it collects gas while also blocking a vent port 127. In a second configuration, the first valve 116a simply directs the split/purge gas to the vent 127 at which the gas exits the system, while blocking any flow to the bladder. The expulsion of the split/purge gas out of the bladder 120 may be controlled by a second 3-way valve 116b installed between a bladder compartment 118 and a source of pressurized air (or gas) source 122, such as an air compressor, a laboratory air line or a pressurized cylinder of air or other gas. Bladder 120 is enclosed in a bladder compartment 118 which is occasionally pressurized by means of the pressurized gas source 122. In a first configuration, the second valve 116b allows gas external to the bladder 120 to exit via port 124 during times when gas is being collected, that is to say when the first valve 116a is in its first configuration. At the same time, the valve 116b prevents the gas source 122 from pressurizing the compartment 118. In a second configuration, the second valve 116b allows gas from source 122 to pressurize the bladder 120 while blocking port 124. This second configuration is applied during the time interval in which valve 116a is in its second configuration thereby allowing collected split/purge gas to be displaced from the bladder into the collection reservoir 129.

During operation of the system 100, the bladder 120 repeatedly inflates, at substantially atmospheric pressure, with gas collected from the split-vent and purge-vent. Bladder compression periods alternate with the bladder inflation periods. During bladder compression periods, the valve 116a is placed into its second configuration (so as to interrupt fluid communication between the split and septum purge vents and the bladder and direct the split/purge gas to the vent 127). Compartment 118 is then pressured so as to compress the bladder 120 and thereby force collected gas quickly out of the bladder to a reservoir 129. A one-way check valve 126 installed between the bladder 120 and the reservoir 129 prevents back flow of collected gas out of the reservoir. During periods of bladder inflation, a controller (not shown) ensures that the pressurized air source 122 does not deliver pressurized air or gas to the bladder compartment 118 and that the second valve 116b allows gas external to the bladder to exhaust through the pump vent 124. The bladder 120 preferably comprises a flexible gas barrier membrane material such as a film or sheet made from polymers of vinyl fluoride (e.g., Tedlar®) or a low permeability metal foil-polymer laminate film such as PAKVF4 from sorbentsystems.com.

Initial injection of a sample may lead to an initial high concentration pulse of volatile solvents. Thus, during this initial injection period, the valve 116a may be maintained in its second or "vent" configuration, thereby allowing volatile solvents and matrix components to vent without undue contamination of collected helium. It is also desirable to maintain valve 116a in this condition during the injection period, so that the small albeit significant backpressure of the collection bladder does not adversely effect the split vent flow rate for split mode injections. At a predetermined time interval subsequent to injection, a GC timed event causes the valve 116a to enter its first or "collect" configuration, thereby enabling split/purge gas to be collected at near atmospheric pressure in the bladder 120 contained in the bladder compartment 118. When a sensor (not shown) detects a bag-full condition, or when a predetermined time interval has elapsed, the first valve 116a is placed in its second or "vent" configuration so as to prevent flow from the chromatograph 108 to the bladder 120 and the second valve 116b is placed in its second or "compress" configuration, thus causing collected helium to be displaced from the bladder 120 into the collection reservoir 129. The sensor may comprise an optical sensor or, alternatively, may comprise a switch, such as a reed switch, that is activated by proximity to the membrane under a bag-full condition. This "bag full" condition is preferably one in which a pair of membranes are mounted within a circular framework and allowed to flex without undue crinkling of the membrane structure about its periphery. This allows for long lifetime of the membrane.

After a predefined time interval, the bladder compression described above is stopped by placing valve 116b in its first or "de-compress" configuration. The collected pressurized gas is then allowed to bleed through a flow restrictor 130 and one or more chemical traps, filters or reactors shown generally at 132

The use of a gas barrier membrane, as described above, allows collection of gas at near atmospheric pressure without undue disturbance of the regulation of the split and purge control of the carrier module. This is possible since the small pressure differential imposed is not applied during the injection period where split flow regulation can be critical e.g. split mode injections. The membrane is allowed to flex within its elastic limit under the influence of pressurized gas. Since the membrane is flexible, substantially equivalent pressure is maintained across the membrane, resulting in long lifetime.

The chemical traps, filters or reactors 132, examples of which are provided below, comprise a purification portion of the system 100 and remove, destroy or render harmless (in an analytical sense) contaminants in the collected gas. Such contaminants may include water, oxygen, traces of solvents used to dissolve or dilute analytes, traces of the analytes or other hydrocarbon compounds. The purified helium exiting the purification portion of the system then re-joins the gas line leading to the carrier gas inlet of the gas chromatograph 108. When sufficient gas pressure is generated in the reservoir 129, the main helium gas supply 101 is closed off by virtue of the higher pressure acting on regulator 102 such that carrier gas is completely provided from the reclamation system. As helium is lost through the GC column or split off during injection, the pressure reduction is compensated by regulator 102 to re-establish the working volume of gas. The flow restrictor 130 may comprise a granular or porous gas permeable frit, or comprise an orifice or capillary tube. The flow restrictor serves to dampen surges in the delivered pressure to the pressure controller of the gas chromatograph 108 as well as to limit the flow rate through the chemical trap or reactor 132 so that efficient contaminant removal ensues.

FIG. 2a illustrates a second system 150 in accordance with the present teachings which represents an improved variation relative to the system 100 (FIG. 1). In the system 150, the chemical trap(s), or filter(s) 135 are optionally provided with a heating element 133 which can be used to heat the chemical trap to a predetermined temperature in order to desorb contaminants which have been removed from the harvested helium. A third 3-way valve 116c can be positioned to selectively block the incoming helium from reservoir 129 and allow the outgassing of the desorbed contaminants from chemical trap 135 through a vent following a second flow restrictor 130b. At the same time, the 3-way valve 116c and a fourth 3-way valve 116d can be selectively positioned so as to provide a low backflush flow rate of helium through flow restrictor 130c.

Dotted arrows in the figures represent the back flush flow during times when valves 116c and 130c are in their back flush positions. The valve 116d may be configured so as to provide an alternate path for the back-flowing clean helium purge gas that bypasses a portion of the path used for the reclaimed gas. This optional alternate path enables the back-flush purge gas to pass through a third flow restrictor 130c so as to stabilize vacuum conditions within the (optionally heatable) chemical trap (e.g. molecular sieve) module 135 when an optional vacuum pump 131 is employed. The optional vacuum pump 131 can be used to assist in efficient desorption of the trap by applying vacuum during the desorption time interval when the trap is heated. This also allows for minimizing the wasted helium as only a few sccm of helium are required for an efficient purge without ill effects caused by air diffusion back to the trap. The vacuum pump 131 can be part of an existing GCMS vacuum system, adding these advantages with little or no cost increase.

FIG. 2b is a schematic illustration of a third gas chromatograph system 300 in accordance with the present teachings which offers an improved variation relative to the system 150. The system 300 shown in FIG. 2b is similar, in most aspects, to the system 150, except that the purification system comprises a pair of optionally heatable chemical traps 135. Thus, the system 300 comprises a fifth valve 116e that is able to switch between the two trap lines. The second trap line of the system 300 comprises a sixth valve 116f, a fourth flow restrictor 130d, an optional second vacuum pump 131, a fifth flow restrictor 130e, a seventh valve 116g and a second optionally heatable chemical trap 135. These components are configured in a parallel arrangement to the corresponding components of the first trap line already discussed with reference to FIG. 2A. This embodiment allows one chemical trap to actively purify the incoming recycled helium while the other trap is being regenerated. Trap selection is made in accordance with the positioning of the additional valve 116e. The embodiment of FIG. 2b allows for continuous operation of a GC or GCMS without interruption, since the regeneration can occur on a run-to-run basis. The chemical trap modules 135 may comprise a molecular sieve material such as a fine particulate activated charcoal which may adsorb many types of chemical contaminants. Alternatively, such molecular sieve material may include one or more of other common molecular sieve materials such as aluminosilicate minerals, clays, zeolites, or efficient synthetic porous polymers such as Tenax®, Carbosieve™, Carboxen™ etc. The sorption materials or trap modules 135 may be tailored based on the sample matrix e.g. gasses or solvents which may be present or employed to dilute the matrix. Breakthrough volumes of many common organic compounds versus various sorbents have been published in the literature, and can be obtained for example from Scientific Instrument Services, Ringoes N J. Appropriate desorption temperatures for the various sorbents are also available.

FIG. 3 is a schematic illustration of a fourth gas chromatograph system 450 in accordance with the present teachings. The system 450 shown in FIG. 3 is similar, in most aspects, to the system 150 shown in and already discussed in reference to FIG. 2a, except that the system 450 comprises, in addition to a chemical trap module 135, a pyrolysis furnace 132a. The pyrolysis furnace 132a is used to cause thermal breakdown of impurities which may have permeated the molecular sieve trap of the gas stream, possibly in the presence of a catalyst such as a nickel tube or powdered Ni metal, within a tube passing through a heater. This results in pyrolysis breakdown products which are retained in the heated tube as carbonaceous deposits or emanate as low molecular weight gasses (e.g. formaldehyde) which are subsequently trapped, purged or back flushed from the system as described previously.

The back-flush capabilities of the systems 150, 300 and 450 (FIGS. 2a, 2b and 3) permit periodic cleansing of a molecular sieve material of the chemical trap modules 135 so as to re-generate the adsorptive capabilities of this material, subsequent to an analysis or following several analytical cycles (e.g. daily). If heaters 133 are included, the heatable chemical trap module(s) 135 can be heated during the back flush to facilitate de-sorption of adsorbed contaminants so that they are removed from the system. During such operation, the valve(s) 116c, 116f are configured so that the contaminant-bearing purge gas is directed to the vent line. The optional vacuum pump(s) 131 may be employed during this operation to aid in the rapid evolution of trapped contaminants and enable regeneration using only small amounts of helium. If the chromatograph 108 comprises a portion of a gas chromatography/mass spectrometry (GCMS) system, the vent line may be directed to an existing vacuum pump of the mass spectrometer.

Figure 5:
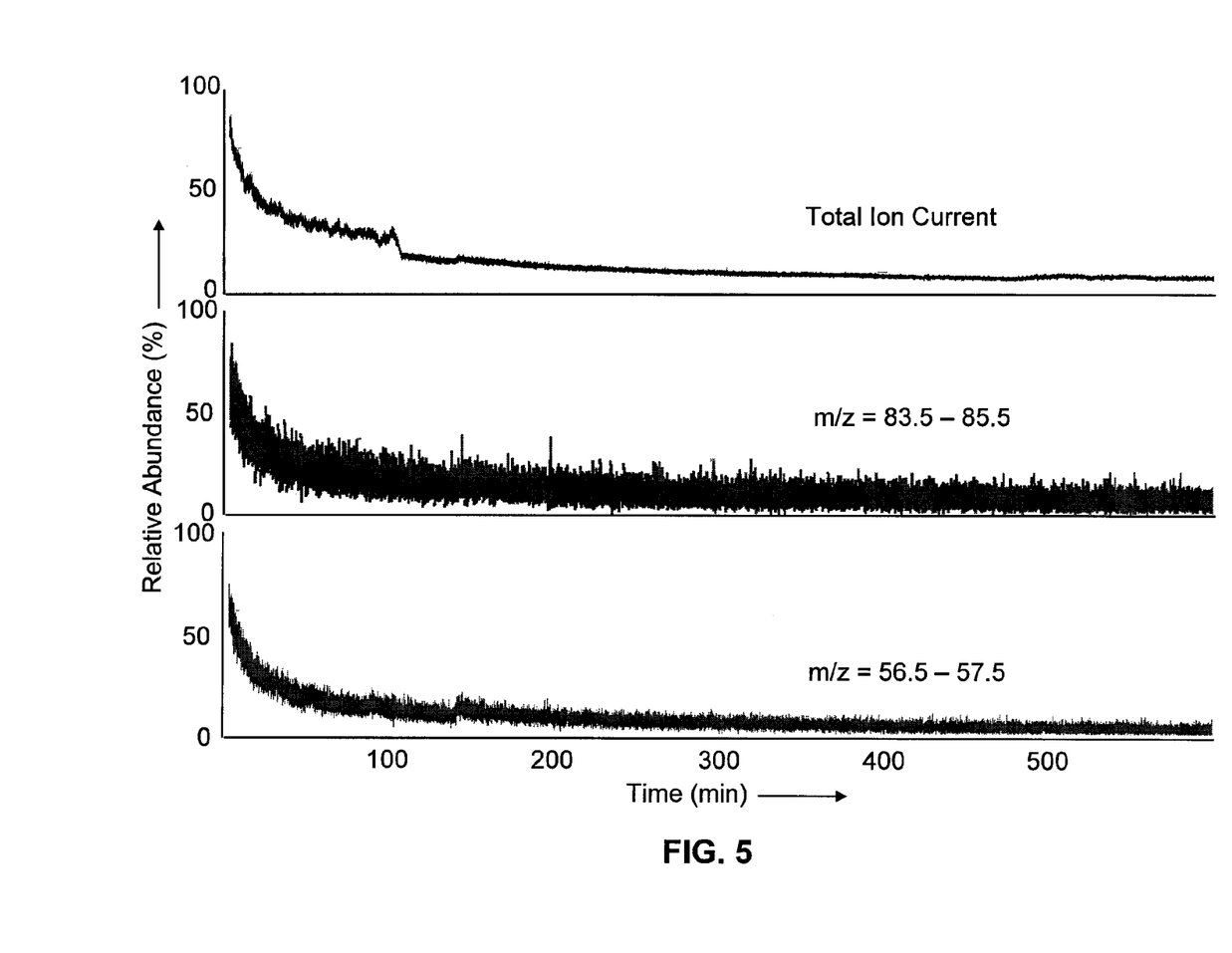
FIG. 5 is data collected which shows the breakthrough time of a 1 micro-liter ($\mu$l) injection of methylene chloride/hexane 50:50 mix on a combined Tenax™, activated charcoal, silica gel trap of small dimensions.
Figure 6:
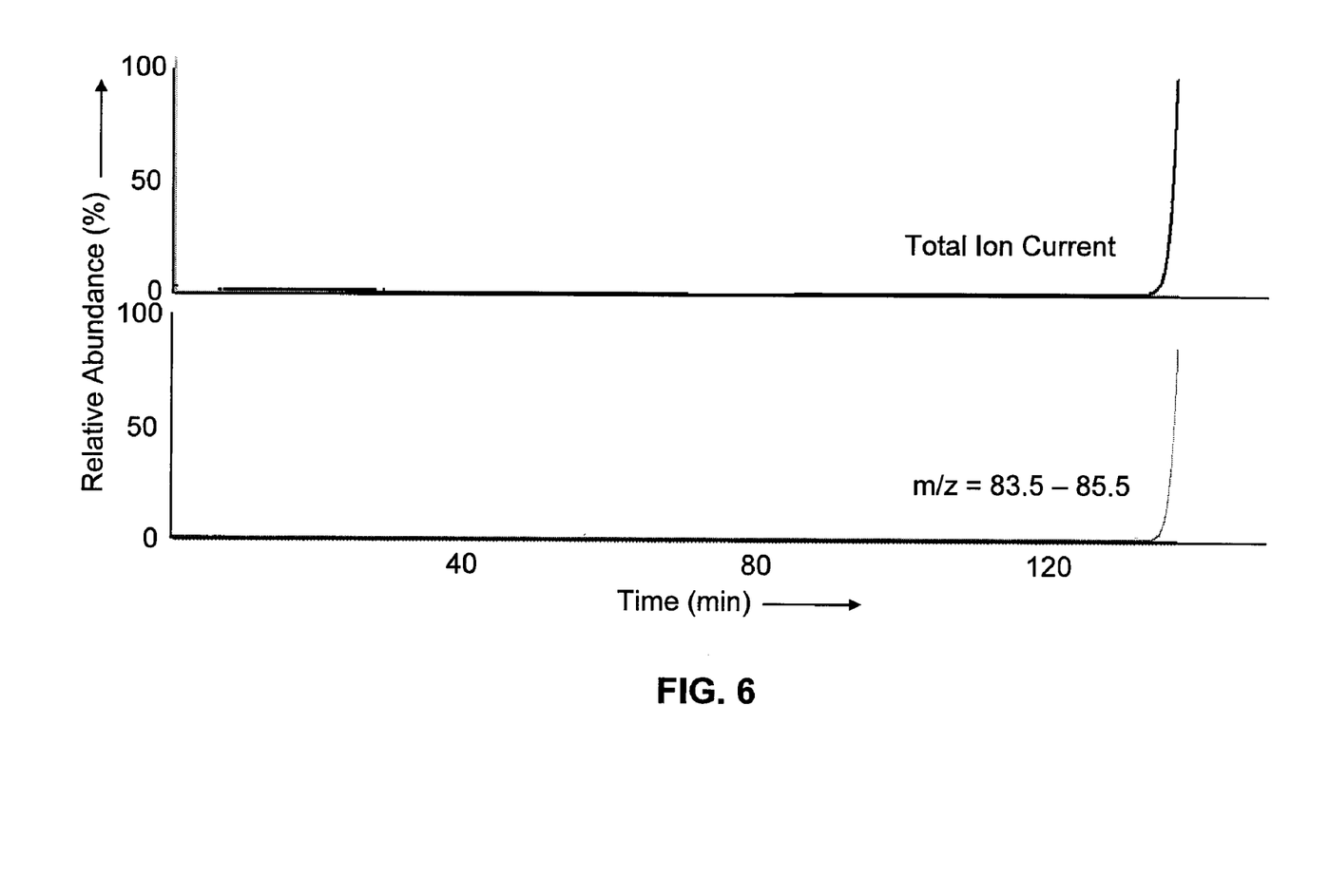
FIG. 6 is data collected which shows the breakthrough time of multiple 1 $\mu$l injections of methylene chloride on the same trap following a regenerative backflush.

It is envisioned that back-flush operations described above will ordinarily be performed at times when the chromatograph 108 is not in operation. However, it is conceivable that the breakthrough time of a molecular sieve trap (particularly a small one) can occur before the completion of a batch of samples. Referring to FIG. 5, data is shown which has been gathered from a "Type C" combined Tenax™, silica gel, activated charcoal trap available from Sigma-Aldrich under Supelco part number 21061-U. This is a trap commonly used for purge and trap analysis of water samples per EPA method 624. A single one microliter injection of a 50:50 methylene chloride/hexane mixture indicates that trap breakthrough does not occur even after 10 hours of operation at 50 sccm helium flow rate. It is known however that trap saturation will impose a premature breakthrough volume. FIG. 6 shows data using the same trap as in FIG. 5, but employing a more typical scenario in which multiple injections occur over a period of time. In this experiment, one microliter injections of methylene chloride were made beginning at time zero and at each ten minute interval thereafter. This data indicates that even with multiple one microliter injections of methylene chloride onto a small trap (the trap dimensions used were ⅛" o.d.×12" length), trap breakthrough does not occur until after fourteen injections and two hours of operation. It is desirable to keep the trap dimensions small in order to effect quick regeneration and to avoid high cost since many of the synthetic high efficiency porous polymers are expensive. Additional on/off valves can be placed following the flow restrictor elements 130b in order to eliminate gas consumption following the backflush operation.

Figure 4:
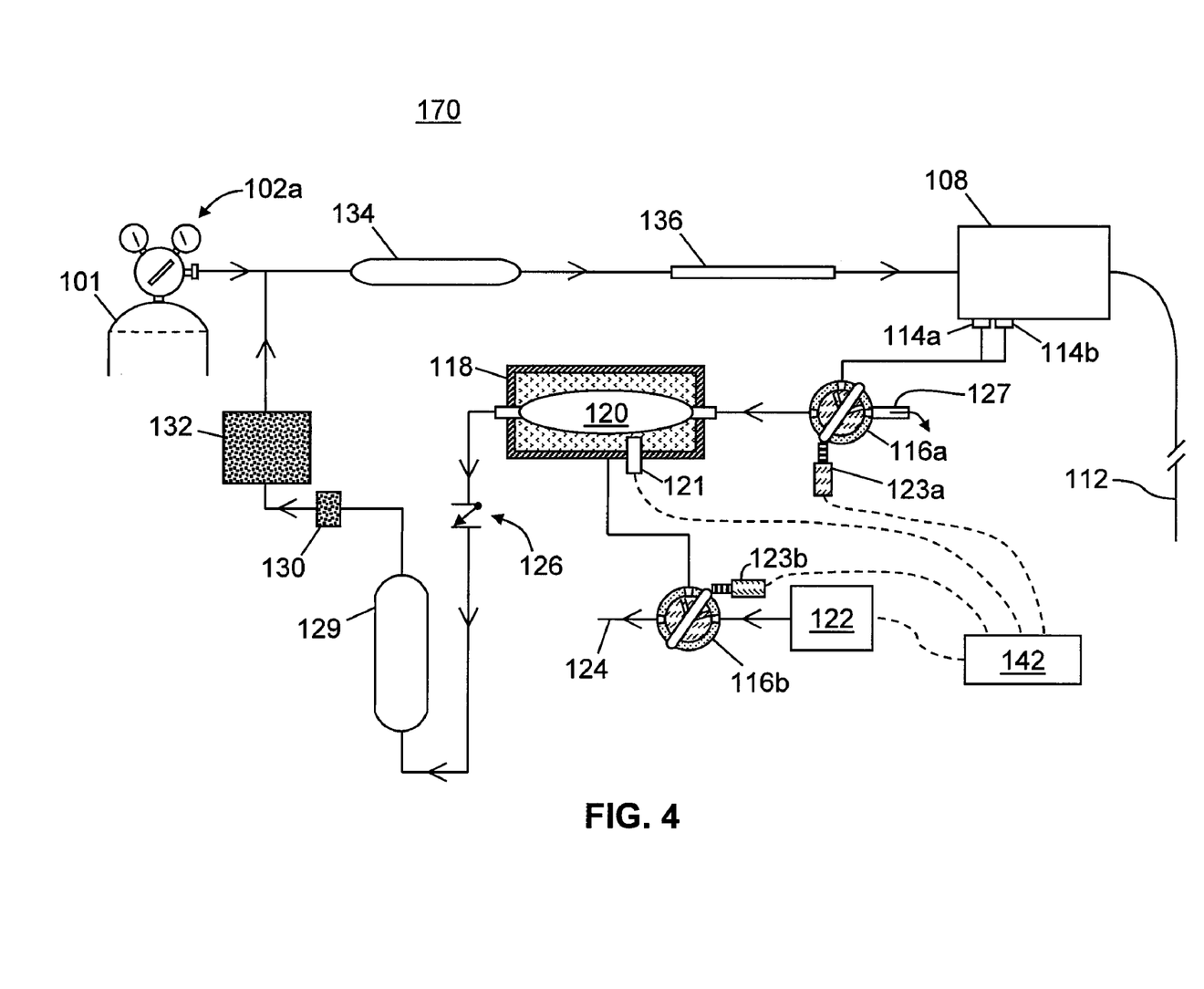
FIG. 4 is a schematic illustration of a gas chromatograph system having automated helium reclamation and recycling capability in accordance with the present teachings.

FIG. 4 schematically illustrates another helium reclamation and recycling system 170 in accordance with the present teachings. FIG. 4 illustrates all of the components previously shown in and discussed with reference to FIG. 1 and also illustrates how the system may be set up for automated operation. Dashed lines in FIG. 4 represent electrical connections or electronic signal connections. A computer or other logical controller 142 is in electrical communication with a sensor 121, a first actuator 123a and a second actuator 123b. Optionally, the computer or other logical controller 142 may also be in electrical communication with the pressurized air or gas source 122. The first 123a and second 123b actuators are configured to mechanically control the operation of the first valve 116a and second valve 116b, respectively.

The sensor 121 of the automated system 170 (FIG. 4), which may be an optical or mechanical sensor, is configured so as to sense when the bladder 120 is sufficiently inflated and to communicate this information to the computer or other logical controller 142. When the bladder is sufficiently inflated, the computer or logical controller 142 sends a signal to the first actuator 123a so as to configure the first valve 116a so as to interrupt fluid communication between the vents 114a, 114b and the bladder 120. The computer or logical controller 142 also sends a signal to the second actuator 123b so as to configure the second valve 116b so as to place the pressurized air or gas source 122 into fluid communication with the interior of the bladder compartment 118. Additionally, if the pressurized air or gas source 122 comprises an air pump, the computer or logical controller 142 may send a signal to energize such air pump. With the valves and pressurized air or gas source 122 so configured, gas pressure applied to the bladder causes the bladder to compress so as to expel any collected gas contained within the bladder interior. Because the valve 116a is configured, at such time, so as to block gas flow from the bladder, all such collected gas is expelled in the direction of the reservoir 129. Further, since the first valve is also configured, at this time so as to direct gas vented from the chromatograph 108 to the vent 127, normal operation of the chromatograph is not impaired.

After a pre-set time during which the bladder is compressed, the computer or logical controller 142 sends a signal to the first actuator 123a so as to configure the first valve 116a so as place the vents 114a, 114b into fluid communication with the bladder 120. The computer or logical controller 142 also sends a signal to the second actuator 123b so as configure the second valve 116b so as to interrupt fluid communication between the pressurized air or gas source 122 and the interior of the bladder compartment 118. Additionally, if the pressurized air or gas source 122 comprises an air pump, the computer or logical controller 142 may send a signal to stop operation of such air pump. Otherwise, the flow of pressurized gas may be simply blocked using a valve such as 116b while gas external to the bladder 120 is directed to a vent 124. In this configuration, the bladder once again collects helium-bearing gas from the septum purge vent 114a and split vent 114b until such time as the sensor once again detects a bag-full condition and the entire cycle is repeated. It is also understood that controller 142 is capable of accepting a disable signal from the gas chromatograph during the injection sequence. This allows controller 142 to stop collection of gas during the injection cycle which allows venting of solvent vapors as well as prevents any back pressure imposed by the bladder collection bag 120.

The systems and methods disclosed herein provide several advantages over conventional gas-chromatograph reclamation systems. A first advantage arises from the fact that, in accordance with the present teachings, vented helium is harvested at atmospheric pressure. This feature enables any electronic pressure controls of the gas chromatograph to be operated with little or no disturbance to or modification of their functions. The reclamation features and methods described herein can thereby be applied to virtually any existing gas chromatograph including both stand-alone and GC-MS installations. A second advantage is that the systems described herein offer a low cost implementation which allows them to be cost competitive relative to hydrogen generators without the associated explosion risk or analytical deficiencies. A third advantage relates to the fact that the present teachings provide for thermal back flushing of the primary trap (particularly into a turbo pump inter-stage or mechanical pump of a GC-MS system). This feature allows efficient and rapid regeneration without excessive consumption of the gas being regenerated. Additionally, the fore pressure of the mechanical pump can be monitored during the desorption cycle in order to provide a semi-quantitative determination of total adsorbed contaminants. Finally, the present teachings provide for self examination of the gas stream. As combined with GCMS, this could include examination of the helium at any point in the recirculation process, including the back flush composition. Additional hardware could be added as necessary for direct sampling to the ion source of a mass spectrometer (for instance, a fluidic coupling between a vent and the ion source) or via chromatographic focusing prior to GC-MS analysis. This can allow the hardware to automatically bypass recirculation until maintenance is performed e.g. trap replacement. Providing the trap influent with a low molecular weight dopant such as a volatile non-interfering chemical species emanating from a permeation tube, or monitoring the accumulation of permanent gas species or pyrolysis products can be used as an indicator for trap breakthrough. The monitoring of the concentration in the analysis can be used as a trigger for initiation of a regeneration cycle (e.g., a total system evacuation or purge cycle) or be used to trigger a bypass or switch to an alternate trap.

The discussion included in this application is intended to serve as a basic description. Although the present invention has been described in accordance with the various embodiments shown and described, one of ordinary skill in the art will readily recognize that there could be variations to the embodiments and those variations would be within the spirit and scope of the present invention. The reader should be aware that the specific discussion may not explicitly describe all embodiments possible; many alternatives are implicit.

As one example of how modifications may be made, it is noted that the specific configurations or placements of valves, gas flow lines and other components shown in the accompanying FIGS. 1-3 is for instructional and example purposes only and one of ordinary skill in the art could envision many minor modifications to these configurations while still maintaining the essence of the invention. As a second example, it is noted that, although the act of compressing a flexible bladder in order to expel collected gas from the bladder interior has been described as being performed, in a simple and straightforward way, by applying elevated air or gas pressure to the bladder exterior, many other compression mechanisms may be envisioned. For instance a bladder containing collected gas could be disposed between two anvils, plates, arms or jaws which move towards one another, thereby physically squeezing the bladder in order to effect bladder compression and gas expulsion. Alternatively, the bladder could be disposed between two rollers or between a single roller and another hard surface, the movement of the roller along a length of the bladder causing expulsion of gas stored therein.

In a broader sense, the bladder itself may be considered as one member of a general class of variable-volume gas storage systems. Another obvious example of a member of this class which may accomplish the same functions described herein would be a piston-in-cylinder arrangement, as in an internal combustion engine. The piston would be able to slide within the associated cylinder along a gas-tight but low friction seal. Entry of helium-bearing gas, through a valve or port, into the chamber formed by the cylinder and piston would cause the piston to move outward so as to expand the chamber volume without a large increase in internal pressure. Alternatively, the position of the piston could be altered by using a mechanical drive mechanism in response to a monitored pressure in order to keep the split and purge exit ports at substantially atmospheric pressure. Later, to expel the gas, an external force could be applied to the piston so as to force it into the cylinder so as to expel the gas through the same or a different valve or port. Additionally, a gas membrane structure as described previously could be immersed in a hydraulic fluid such as mineral oil. The hydraulic fluid could be compressed mechanically or pneumatically with the advantage of lower compressed gas consumption. This implementation could also incorporate membranes with greater elasticity which otherwise have poor gas permeation qualities. The hydraulic fluid could thus serve a second function to minimize oxygen gas diffusion through the membrane.

Accordingly, many modifications may be made by one of ordinary skill in the art without departing from the spirit, scope and essence of the invention. Neither the description nor the terminology is intended to limit the scope of the invention. Note that any publications, patents or patent application publications mentioned in this specification are explicitly incorporated by reference in their respective entirety.

What is claimed is:

1. A system for collecting, re-pressurizing, purifying and re-using helium gas used as a carrier gas for a gas chromatograph, the system comprising:
   (i) a flexible bladder comprising a bladder interior, the bladder interior fluidically coupled to at least one of a split vent and a septum purge vent of the gas chromatograph so as to receive helium-bearing gas output from the at least one of said vents;
   (ii) a compartment comprising a compartment interior within which the bladder is contained;
   (iii) a source of pressurized air or gas fluidically coupled to the compartment interior and operable so as to supply said pressurized air or gas into the compartment interior so as to compress the flexible bladder containing the helium-bearing gas;
   (iv) a gas reservoir fluidically coupled to the bladder interior so as to receive the helium bearing gas from the interior of the compressed bladder; and
   (v) at least one gas purification module comprising a pyrolysis furnace that is fluidically coupled to the gas reservoir so as to receive the helium-bearing gas from the gas reservoir and operable to remove gas components other than helium from the helium-bearing gas, wherein an output of the at least one gas purification module is fluidically coupled to a carrier gas inlet of the gas chromatograph.

2. A system as recited in claim 1, wherein the at least one gas purification module further comprises a molecular sieve module.

3. A system for collecting, re-pressurizing, purifying and re-using helium gas used as a carrier gas for a gas chromatograph, the system comprising:
   (i) a flexible bladder comprising a bladder interior, the bladder interior fluidically coupled to at least one of a split vent and a septum purge vent of the gas chromatograph so as to receive helium-bearing gas output from the at least one of said vents;
   (ii) a compartment comprising a compartment interior within which the bladder is contained;
   (iii) a source of pressurized air or gas fluidically coupled to the compartment interior and operable so as to supply said pressurized air or gas into the compartment interior so as to compress the flexible bladder containing the helium-bearing gas;
   (iv) a gas reservoir fluidically coupled to the bladder interior so as to receive the helium bearing gas from the interior of the compressed bladder;
   (v) at least one gas purification module fluidically coupled to the gas reservoir so as to receive the helium-bearing gas from the gas reservoir and having an output that is fluidically coupled to a carrier gas inlet of the gas chromatograph, the at least one gas purification module operable to remove gas components other than helium from the helium-bearing gas and comprising a molecular sieve module having an input end configured so as to receive the helium-bearing gas from the gas reservoir and an output end;
   (vi) a source of purified helium gas fluidically coupled to the output end of the molecular sieve module for providing a flow of the purified helium gas into the molecular sieve module through the output end; and
   (vii) a second valve fluidically coupled between the reservoir and the input end of the molecular sieve module and configurable so as to receive the flow of the purified helium gas from the input end of the molecular sieve module and to direct said flow of the purified helium gas to an exhaust vent.

4. A system as recited in claim 3, further comprising:
   (viii) a heater coupled to the molecular sieve module.

5. A system as recited in claim 3, further comprising:
   (viii) a vacuum system fluidically coupled to the exhaust vent.

6. A system as recited in claim 5 wherein the vacuum system is a mass spectrometer vacuum system.

7. A system as recited in claim 3, wherein the exhaust vent is fluidically coupled to an ion source of a mass spectrometer.

8. A system as recited in claim 3, wherein the source of purified helium gas is configured so as to supply a second flow of the purified helium gas to a carrier gas inlet of the gas chromatograph.

9. A system for collecting, re-pressurizing, purifying and re-using helium as used as a carrier gas for a gas chromatograph, the system comprising:
   (i) a flexible bladder comprising a low permeability metal foil-polymer laminate film and comprising a bladder interior, the bladder interior fluidically coupled to at least one of a split vent and a septum purge vent of the gas chromatograph so as to receive helium-bearing gas output from the at least one of said vents;
   (ii) a compartment comprising a compartment interior within which the bladder is contained;
   (iii) a source of pressurized air or gas fluidically coupled to the compartment interior and operable so as to supply said pressurized air or as into the compartment interior so as to compress the flexible bladder containing the helium-bearing gas;

(iv) a gas reservoir fluidically coupled to the bladder interior so as to receive the helium bearing gas from the interior of the compressed bladder; and
(v) at least one gas purification module fluidically coupled to the gas reservoir so as to receive the helium-bearing gas from the gas reservoir and operable to remove gas components other than helium from the helium-bearing gas,
wherein an output of the at least one gas purification module is fluidically coupled to a carrier gas inlet of the gas chromatograph.

10. A system for collecting, re-pressurizing, purifying and re-using helium gas used as a carrier gas for a gas chromatograph, the system comprising:
(i) a flexible bladder comprising a bladder interior, the bladder interior fluidically coupled to at least one of a split vent and a septum purge vent of the gas chromatograph so as to receive helium-bearing gas output from the at least one of said vents;
(ii) a compartment comprising a compartment interior within which the bladder is contained;
(iii) a source of pressurized air or gas fluidically coupled to the compartment interior and operable so as to supply said pressurized air or gas into the compartment interior so as to compress the flexible bladder containing the helium-bearing gas;
(iv) a gas reservoir fluidically coupled to the bladder interior so as to receive the helium bearing gas from the interior of the compressed bladder;
(v) at least one gas purification module fluidically coupled to the gas reservoir so as to receive the helium-bearing gas from the gas reservoir and having an output that is fluidically coupled to a carrier gas inlet of the gas chromatograph, the at least one gas purification module operable to remove gas components other than helium from the helium-bearing gas and comprising a first molecular sieve module comprising a first input end and a first output end;
(vi) a first valve fluidically coupled between the gas reservoir and the at least one purification module;
(vii) at least one additional gas purification module fluidically coupled to the first valve and operable to remove gas components other than helium from the helium-bearing gas and comprising a second molecular sieve module comprising a second input end and a second output end;
(viii) a source of purified helium gas fluidically coupled to the first output end and the second output end for providing a flow of the purified helium gas into either the first molecular sieve module through the first output end or the second molecular sieve module through the second output end;
(ix) a second valve fluidically coupled between the first valve and the first input end of the first molecular sieve module; and
(x) a third valve fluidically coupled between the first valve and the second input end of the second molecular sieve module,
wherein the first valve is configurable to direct the helium-bearing gas either to the at least one purification module or to the at least one additional gas purification module and wherein an output of the at least one additional gas purification module is fluidically coupled to a carrier gas inlet of the gas chromatograph.

11. A system for collecting, re-pressurizing, purifying and re-using helium gas used as a carrier gas for a gas chromatograph, the system comprising:
(i) a flexible bladder comprising a bladder interior, the bladder interior fluidically coupled to at least one of a split vent and a septum purge vent of the as chromatograph so as to receive helium-bearing gas output from the at least one of said vents;
(ii) a compartment comprising a compartment interior within which the bladder is contained;
(iii) a source of pressurized air or gas fluidically coupled to the compartment interior and operable so as to supply said pressurized air or gas into the compartment interior so as to compress the flexible bladder containing the helium-bearing gas;
(iv) a gas reservoir fluidically coupled to the bladder interior so as to receive the helium bearing gas from the interior of the compressed bladder;
(v) at least one gas purification module fluidically coupled to the gas reservoir so as to receive the helium-bearing gas from the gas reservoir and operable to remove gas components other than helium from the helium-bearing gas;
(vi) a first actuator operable so as to adjust the fluidic coupling between the bladder interior and the at least one of the split vent and the septum purge vent;
(vii) a second actuator operable so as to adjust the fluidic coupling between the compartment interior and the source of pressurized air or gas;
(viii) a sensor coupled to the flexible bladder for sensing a degree of inflation of the flexible bladder; and
(ix) an electronic controller electrically coupled to the first and second actuators and to the sensor, wherein the electronic controller is operable so as to send control signals to the first and second actuators in response to a signal received from the sensor,
wherein an output of the at least one gas purification module is fluidically coupled to a carrier gas inlet of the gas chromatograph.

12. A method for re-claiming helium gas output from a split vent or a septum purge vent of a gas chromatograph, comprising:
(a) receiving a flow of a gas mixture including the helium gas into the interior of a flexible bladder from at least one of the split vent and the septum purge vent;
(b) compressing the flexible bladder so as to expel the gas mixture from the bladder interior into a reservoir; and
(c) causing the gas mixture to flow from the reservoir through a pyrolysis furnace of a gas purification module, the gas purification module removing gas components other than helium from the gas mixture flowing therethrough so as to recover purified helium.

* * * * *